(12) United States Patent
Schattenmann et al.

(10) Patent No.: US 7,339,069 B2
(45) Date of Patent: Mar. 4, 2008

(54) CONTINUOUS PROCESS FOR PREPARING SIOC-CONTAINING COMPOUNDS

(75) Inventors: Wolfgang Schattenmann, Burghausen (DE); Georg Loher, Braunau (AT)

(73) Assignee: Wacker Chemie AG, Munich (DE)

( * ) Notice: Subject to any disclaimer, the term of this patent is extended or adjusted under 35 U.S.C. 154(b) by 214 days.

(21) Appl. No.: 11/333,669

(22) Filed: Jan. 17, 2006

(65) Prior Publication Data

US 2006/0167297 A1 Jul. 27, 2006

(30) Foreign Application Priority Data

Jan. 27, 2005 (DE) ...................... 10 2005 003 898

(51) Int. Cl.
*C07F 7/08* (2006.01)

(52) U.S. Cl. ...................................... 556/471

(58) Field of Classification Search ...................... None
See application file for complete search history.

(56) References Cited

U.S. PATENT DOCUMENTS

| | | | |
|---|---|---|---|
| 2,661,348 A | 12/1953 | Welsh et al. | |
| 2,758,124 A | 8/1956 | Schwenker et al. | |
| 3,489,782 A | 1/1970 | Pruvost et al. | |
| 3,792,071 A | 2/1974 | Nitzsche et al. | |
| 4,209,454 A | 6/1980 | Graf et al. | |
| 4,298,753 A | 11/1981 | Schinabeck et al. | |
| 4,506,087 A | 3/1985 | Fischer et al. | |
| 5,223,636 A | 6/1993 | Koshimura et al. | |
| 6,150,550 A | 11/2000 | Bade et al. | |
| 6,767,982 B2 | 7/2004 | Standke et al. | |
| 2002/0086907 A1 | 7/2002 | Standke et al. | |

FOREIGN PATENT DOCUMENTS

| | | |
|---|---|---|
| DE | 854 708 | 11/1952 |
| DE | 953 661 | 12/1956 |
| DE | 954 198 | 12/1956 |
| DE | 1 302 773 | 8/1972 |
| DE | 24 15 331 | 10/1975 |
| EP | 0 924 215 A2 | 6/1999 |
| EP | 1 205 505 A2 | 5/2002 |
| GB | 1192506 | 5/1970 |

OTHER PUBLICATIONS

Abstract Corresponding to DE 854 708.
Derwent Abstract Corresponding to DE 1 302 773.
Derwent Abstract Corresponding to DE 24 15 331.

*Primary Examiner*—Samuel A Barts
(74) *Attorney, Agent, or Firm*—Brooks Kushamn P.C.

(57) ABSTRACT

A process for continuously preparing compounds containing SiOC groups, in which chlorosilane(s) are partially reacted with alcohol and optionally also with water in a prereactor, and the partial reaction product therefrom is fed to a first reaction unit comprising a column, reacted with alcohol and optionally water to give a crude product which still comprises volatile constituents, and the crude product is transferred to a second reaction unit comprising a column in which alcohol is additionally introduced, and freed there of volatile constituents, optionally in the presence of an unreactive organic solvent, the desired end product being removed at the lower end of the second reaction unit.

8 Claims, No Drawings us7339069b2

CONTINUOUS PROCESS FOR PREPARING SIOC-CONTAINING COMPOUNDS

BACKGROUND OF THE INVENTION

1. Field of the Invention

The invention relates to a continuous process for preparing SiOC-containing compounds.

2. Background Art

The preparation of SiOC-containing compounds by means of column technology, in particular alkoxysilanes and alkoxy-rich silicone resins, has been known for some time. Starting from chlorosilane(s), alkoxylation takes place in a column and its bottom. In the case of alkoxy-rich silicone resins, water is metered in a controlled manner in deficiency based on the SiCl units metered in.

U.S. Pat. No. 3,792,071 A1 describes a process for continuously preparing alkoxysilanes or alkoxypolysiloxanes, in which, in a column with reflux condenser, chlorosilane is fed in at the top, gaseous alcohol fed to the lower third, and water at any point, the column temperature being at least 0.5° C. above the boiling point of the alcohol. The material flowing out of the lower end of the column is freed of alcohol in a circulating evaporator, and the alcohol then recycled into the column.

As a further development of this process, U.S. Pat. No. 4,298,753 A1 describes a process for continuously preparing alkoxysilanes or alkoxypolysiloxanes, in which, in a first reactor, for example, a stirred tank or stirred reactor, including U-shaped or annular reactors, with reflux condenser, chlorosilane, 0.5 to 0.9 eq. of alcohol/Si—Cl, and optionally water is introduced concurrently in liquid form and mixed, the effluent liquid being fed into the top of a column used as a 2nd reactor. Gaseous alcohol for the reaction of the remaining SiCl groups is metered into the lower third of the column, optionally in addition to water at any point, and the product is removed below the alcohol feed.

A further process for continuously preparing monomeric or oligomeric alkoxysilanes is described by U.S. Pat. No. 4,506,087 A1. In a reactor with an attached column, chlorosilane and optionally water are metered in liquid form into the reactor, and alcohol is metered in gaseous form into the lower section of the column. Condensed alcohol leaving the column at the top is introduced into the reactor. The product leaving the reactor is fed to the top of the column and the end product is withdrawn at the lower end of the column.

U.S. Pat. No. 6,767,982 B2 discloses a further process for the continuous preparation of a mixture of organoalkoxysiloxanes. In a first stage (stirred tank or reaction column), at least one organotrichlorosilane is reacted with water (0.59 to 0.95 mol based on silane) and alcohol (0.5 to 100 mol based on silane) at a temperature of from 0 to 150° C., HCl is removed simultaneously, and the crude product, after a delay time of from 0.5 to 180 min, is transferred partly into a reaction distillation column of the second process stage. Alcohol is fed into the lower section of this column and volatile components are removed as the overhead product. The desired organopolysiloxanes are obtained at a temperature of from 50 to 200° C. in the bottoms and are freed of residual chloride in an aftertreatment step. The volatile components removed as the top product are, after condensation, recycled into the first reaction unit.

It is evident from the prior art that a continuous process utilizing at least one column unit is particularly advantageous for preparing SiOC-containing compounds. However, the productivity of these processes is restricted by the limited throughput of each column unit, and the throughput of the column in which the majority of the HCl is formed limits the entire process. In this column, a stream of a liquid phase (alkoxysilane/part-alkoxylate formed) is present from the top downward and, at the same time, a stream of a gas phase (HCl) from the point of formation at the top of the column. In the event of too strong a stream of the gas phase, a pressure is generated which is so great that the mobile liquid phase no longer moves downward owing to gravity but rather is discharged at the top of the column.

SUMMARY OF THE INVENTION

It is an object of the present invention to increase the space-time yield of a process for continuously preparing compounds containing SiOC groups by a process which utilizes two column units. These and other objects are achieved by a process in which a reaction mixture, in a first reaction unit comprising a column, is reacted with alcohol and optionally water to give a crude product which still comprises volatile constituents and is transferred to a second reaction unit comprising a column in which alcohol is additionally introduced and the product freed there of the volatile constituents, optionally in the presence of an unreactive organic solvent. The desired end product is removed at the lower end of the second reaction unit. The reaction mixture fed to the first reaction unit is prepared in a prereactor, by partially reacting a chlorosilane with alcohol and optionally with water.

DETAILED DESCRIPTION OF THE PREFERRED EMBODIMENT(S)

As a result of the inventive process employing a prereactor, a distinctly higher space-time yield is obtained, since a majority of the hydrogen chloride formed, which limits the throughput of the first reaction unit, is instead formed in the prereactor and removed, thus deburdening the downstream column.

The alcohol, with or without water, which is utilized in the prereactor to partially convert the chlorosilane, is preferably the distillate of the second reaction unit which is recycled into the prereactor as distillate or gas. The distillate may be admixed with additional alcohol and/or water, in the prereactor or before introduction into the prereactor, and preferably, in the case of additional water metering, homogenized by means of a short mixing zone. Preference is given to pure alkoxylation in the prereactor without condensation in the prereactor.

This preferred embodiment of the process, in which the distillate of the second reaction unit is introduced into the prereactor and not, as usual, into the first reaction unit has the following advantages: first, the contents of the bottom of the first reaction unit generally have a high proportion of volatile compounds, substantially alcohol. This alcohol is thus utilized additionally for the reaction in the prereactor. In particular, this is shown in the preparation of alkoxypolysiloxanes which, in addition to the alkoxylation, are also subjected to a hydrolysis, as is shown by the examples. Secondly, the alcohol added is utilized in two ways. Firstly, it is utilized in countercurrent in the second reaction unit in order to free the crude product of volatile impurities, especially of adhering hydrogen chloride, and to postreact any Si—Cl units still present. In addition, the alcohol is made available as a reactant in the prereactor and thus to deburden the reaction unit 1.

The chlorosilanes uses are preferably those chlorosilanes which have been used conventionally for the preparation of alkoxysilanes or organopolysiloxanes by reaction of chlorosilane with alcohols and optionally water. In particular, these are compounds of the general formula $$R_nSiCl_{4-n}$$

where n may be 0-3 and where

R is hydrogen or identical or different monovalent, substituted or unsubstituted organic radical.

Examples of R are hydrogen and hydrocarbon radicals such as the methyl, ethyl, vinyl, n-propyl, i-propyl, allyl, n-butyl, i-butyl, n-pentyl, i-pentyl, n-hexyl, i-hexyl, cyclohexyl, n-heptyl, n-octyl, i-octyl, hexadecyl, octadecyl, phenyl and tolyl radicals; and also substituted hydrocarbon radicals in which the carbon atoms to which halogen is bonded are in the alpha position or the gamma position to the silicon atom, for example, the gamma-chloropropyl radical; and haloaryl radicals, for example chlorophenyl radicals. Further examples of suitable substituted hydrocarbon radicals are the beta-cyanoethyl radical and the gamma-acryloyloxypropyl radical, and also the gamma-methacryloyloxypropyl radical.

Preference is given to hydrocarbon radicals such as the methyl, ethyl, vinyl, n-propyl, i-propyl, -butyl, i-butyl, n-pentyl, i-pentyl, n-hexyl, i-hexyl, cyclohexyl, n-heptyl, n-octyl, i-octyl, hexadecyl, octadecyl, phenyl and tolyl radicals. Particular preference is given to hydrocarbon radicals such as the methyl, vinyl, n-propyl, -butyl, i-octyl and phenyl radicals. It is also possible to use mixtures of different chlorosilanes.

The alcohols used are preferably hydrocarbon compounds having an alcoholic hydroxyl group which are conventionally used to prepare alkoxysilanes or organopolysiloxanes by reacting chlorosilanes with alcohols and optionally water, and whose boiling point is below that of the alkoxysilanes or organopolysiloxanes to be prepared. Preference is given to alkanols and ether group-containing alkanols having from 1 to 6 carbon atoms, such as methanol, ethanol, beta-methoxyethanol, n-propanol, isopropanol, n-butanol or n-hexanol. Particular preference is given to methanol, ethanol, isopropanol or n-butanol. It is also possible to use mixtures of different alcohols.

If appropriate, an organic solvent may also be included. Useful solvents are all organic solvents. Preference is given to using unreactive organic solvents, for example toluene or xylene.

The hydrogen chloride formed in the process is preferably freed of the condensable fractions at the top of the prereactor and at the top of the first reaction unit, and the condensable fractions are in turn recycled back into the appropriate reaction unit. The hydrogen chloride is thus available as a gas for recovery.

The prereactor may consist, for example, of a stirred tank, a tubular reactor or a loop reactor with or without forced circulation. In the case of a pure alkoxylation reaction, there is no need for forced circulation since the hydrogen chloride formed in the reaction is already sufficient to ensure sufficient circulation and mixing. In the case of additional water metering, preference is given to forced circulation and particular preference to a prereactor with high mixing efficiency, for example a loop reactor.

Preference is given to introducing a liquid chlorosilane into the prereactor, a maximum of 80% of the molar amount of Si-bonded chlorine units being reacted with alcoholic hydroxyl groups and optionally water in the prereactor. The prereactor is preferably operated at a temperature below the boiling point of the chlorosilane or the chlorosilane mixture used.

The partially reacted reaction mixture is transferred to the column of a first reaction unit in which further mixing and reaction of chlorosilane, alcohol and optionally water is effected to give hydrogen chloride gas and a liquid crude product. This can be achieved, for example, by means of an overflow apparatus. The temperature in the column of the reaction unit 1 preferably does not exceed 120° C. More preferably, the temperature in the column does not exceed 100° C.

The liquid crude product is introduced into a column used as a 2nd reaction unit. Alcohol is introduced into the lower third of the second column in order to free the crude product of volatile constituents, especially of adhering hydrogen chloride, in countercurrent, and to postreact any Si—Cl units still present. The temperature in the second reaction unit is restricted only by stability and boiling points of the SiOC compounds formed, the amount and the boiling point of the alcohol used for stripping and, in the presence of a solvent, by its boiling point.

The alcohol can in principle be introduced into all reaction units. The majority of the alcohol is preferably introduced into the second column in countercurrent, in order to free the crude product of volatile constituents, especially of adhering hydrogen chloride, and to postreact any Si—Cl units still present. Preference is given to removing this alcohol at the top of the second column, condensing it and subsequently metering the distillate into the prereactor.

The first and the second reaction unit preferably each consist of a column with a circulation evaporator. The bottoms of the first reaction unit are preferably metered continuously, advantageously at maximum proximity to the top of the second reaction column.

The performance of the process according to the invention will be described below by way of example using an apparatus which has also been used in the examples which follow:

The plant comprises a prereactor and two columns, each with a circulation evaporator. The prereactor is a loop reactor with a centrifugal pump which is controllable with a valve and pumps the liquid contents in circulation with maximum turbulence.

At the lower side, the chlorosilane and the distillate of the second reaction unit are metered into the prereactor. Alcohol and water are optionally metered into the distillate which is homogenized by means of a short mixing zone. The contents of the prereactor are introduced into the first reaction unit by means of an overflow apparatus. At the upper side, the prereactor has an outlet for the hydrogen chloride gas which forms. This gas is freed of condensable fractions by means of a water cooler and subsequently a brine cooler, the condensable fractions being recycled directly back into the prereactor. The hydrogen chloride gas present downstream of the cooler can be recovered or dissolved in water in a scrubber and disposed of as HCl solution. The two downstream reaction units each consist of a circulation evaporator and a column attached thereto. The column of the first reaction unit has, at the top, first a water-operated cooler and then a brine-operated cooler. The distillates obtained there are fed into the first column. The hydrogen chloride gas obtained downstream of the cooler can be recovered or dissolved in water in a scrubber and disposed of as HCl solution. The column of the second reaction unit has, at the top, a water-operated cooler. The volatile constituents condensed there including the gas are recycled into the prereactor as described.

From the circulation evaporator of the first reaction unit, as much reaction mixture is discharged continuously by means of a centrifugal pump as is obtained by the reaction. The reaction mixture from the circulation evaporator of the first reaction unit is introduced to the top, directly below the condensation unit of the second column. From the circulation evaporator of the second reaction unit, product is likewise withdrawn by means of a circulation pump to the degree in which it has been formed.

The examples which follow serve to further illustrate the invention.

EXAMPLE 1

The prereactor with a capacity of 2 l is charged with 2 l of MeSiCl$_3$ (Me=methyl). The 2.5 l circulation evaporator of the first reaction unit with an attached 5 m column with an internal width of 50 mm is charged with 2.250 l of the desired alkoxypolysiloxane consisting of MeSiO$_{3/2}$ units with an ethoxy content of 29% by weight, and 250 ml of ethanol.

The 2.0 l circulation evaporator of the second reaction unit with an attached 5 m column with an internal width of 50 mm is charged with 1.800 l of the desired alkoxypolysiloxane consisting of MeSiO$_{3/2}$ units with an ethoxy content of 29% by weight, and 200 ml of ethanol.

The chlorosilane in the prereactor is circulated by pumping, and heated to 34° C. The reaction units comprising the two columns are heated by means of the circulation evaporator until condensation commences at the top of the second column. Subsequently, the continuous metered additions are started as follows:

2000 g/h of MeSiCl$_3$ are fed into the prereactor. Just above the circulation evaporator of the first reaction unit, 258 g/h of water and ethanol are fed in to such a degree that a constant temperature profile (of 62-73° C.) is obtained in the column (typically: approx. 300 ml/h). The temperature in the prereactor is kept constant at 30-34° C.

In the bottom of reaction unit 1, there is a temperature of approx. 77° C. The crude product is withdrawn constantly from the circulation evaporator to the degree to which it is formed and fed to the top, below the condensation units, of reactor 2.

The temperature in the column of reactor 2 is kept at approx. 73-79° C. The temperature in the circulation evaporator of reactor 2 is approx. 173° C. The condensate from reactor unit 2 is fed into the prereactor at the bottom downstream of the circulation pump on the pressure side. Approx. 1 m above the circulation evaporator of reaction unit 2, 400 ml/h of ethanol are metered in.

From the circulation evaporator of reactor 2, a clear product is removed continuously. To determine the resin quality of this crude product, workup was effected with methods customary for silicone resin. The analysis of the resulting silicone resin gave a viscosity of 25.4 mm$^2$/s at 25° C., an ethoxy content of 29.2% (which corresponds to a molar conversion of the Si—Cl used to Si—OEt of 24.9%) and a molecular weight Mw of 3000 g/mol. (Et=ethyl)

From the prereactor, samples were taken regularly during the continuous reaction in order to determine the SiCl conversion achieved in the prereactor. The analysis was carried out by means of NMR spectroscopy and gave, for Si—Cl, Si—O$_{1/2}$ and Si—OEt, the following molar ratios: Si—Cl/Si—OEt/Si—O$_{1/2}$=46.9/52.6/0.5. The analysis of the prereactor shows by way of example the particular advantage of the inventive reaction, of introducing the distillate of the second reaction unit into the prereactor. On the basis of the stoichiometry of the end product, the maximum possible alkoxylation in the prereactor without a distillate addition of the second reaction unit could not be more than 24.9 mol % (fraction of Si—OEt units based on total SiCl conversion), even taking into account the alcohol which is required for control of the first column and for postreaction and HCl discharge in the second column. However, by virtue of the distillate of the second reaction unit being included in this preferred embodiment of the invention, it is possible, even without condensation, to achieve a high SiCl conversion (greater than 50%). Pure alkoxylation in the prereactor without condensation is preferred owing to the more agreeable reaction. This prereactor design creates a capacity increased by a factor of 2 exclusively via alkoxylation based on HCl removal.

EXAMPLE 2

The prereactor is charged with 2 l of MeSiCl$_3$. The 2.5 l circulation evaporator of the first reaction unit is charged with 2.250 l of the desired alkoxypolysiloxane consisting of MeSiO$_{3/2}$ units with an ethoxy content of 29% by weight, and 250 ml of ethanol.

The 2.0 l circulation evaporator of the second reaction unit is charged with 1800 ml of the desired alkoxypolysiloxane consisting of MeSiO$_{3/2}$ units with an ethoxy content of 29% by weight, and 200 ml of ethanol.

The chlorosilane in the prereactor is pumped in circulation and has a temperature of 34° C. The reaction units comprising the two columns are heated by means of the circulation evaporator until condensation at the top of the second column commences. Subsequently, the continuous metered additions are started as follows:

2000 g/h of MeSiCl$_3$ are fed into the prereactor. Just above the circulation evaporator of the first reaction unit, 215 g/h of water and ethanol are fed in to the degree that a constant temperature profile (of 66-74° C.) in the column is obtained (typically: approx. 300 ml/h). 39 g/h of ethanol and 51 g/h of water are introduced into the distillate stream from the second reaction unit into the prereactor. The temperature in the prereactor is kept at a constant 33° C.

In the bottom of reaction unit 1, the temperature is approx. 77° C. The crude product is withdrawn constantly from the circulation evaporator to the degree in which it is formed and fed to the top, below the condensation units, of reactor 2.

The temperature in the column of reactor 2 is kept at approx. 65-78° C. The temperature in the circulation evaporator of reactor 2 is approx. 175° C. The condensate from reactor unit 2 is fed into the prereactor at the bottom downstream of the circulation pump on the pressure side. Approx. 1 m above the circulation evaporator of reaction unit 2, 200 ml/h of ethanol are metered in.

From the circulation evaporator of reactor 2, a clear product is removed continuously. To determine the resin quality of this crude product, workup was effected with methods customary for silicone resin. The analysis of the resulting silicone resin gave a viscosity of 21 mm$^2$/s, an ethoxy content of 28.2% by weight (which corresponds to a molar conversion of the Si—Cl used to Si—OEt of 23.7%) and a molecular weight Mw of 1800 g/mol.

From the prereactor, samples were taken regularly during the continuous reaction in order to determine the SiCl conversion achieved in the prereactor. The analysis was carried out by means of NMR spectroscopy and gave, for the Si—Cl, Si—O$_{1/2}$ and Si—OEt, the following molar ratios: Si—Cl/Si—OEt/Si—O$_{1/2}$=36.5/52.5/11.0. The analysis of the prereactor here too again shows the particular advantage of this reaction, of introducing the distillate of the second reaction unit into the prereactor. On the basis of the stoichiometry of the end product, the maximum possible alkoxylation in the prereactor without a distillate addition of the second reaction unit could not be more than 23.7 mol % (fraction of Si—OEt units based on total SiCl conversion), even taking account here of the alcohol which is required for control of the first column and for postreaction and HCl discharge in the second column. However, by virtue of the distillate of the second reaction unit being taken into account, it is already possible to achieve high SiCl conversion without condensation (greater than 50%; as in Example 1), exclusively by alkoxylation. The combination of alkoxylation with partial condensation deburdened the downstream column by nearly ⅔ based on HCl removal.

EXAMPLE 3

The prereactor is charged with 2 l of a silane mixture consisting of PhSiCl$_3$ and Me$_2$SiCl$_2$ in a molar ratio of PhSiCl$_3$/Me$_2$SiCl$_2$=2/1. (Ph=phenyl). The 2.5 l circulation evaporator of the first reaction unit is charged with 800 ml of the desired alkoxypolysiloxane consisting of PhSiO$_{3/2}$ and Me$_2$SiO$_{2/2}$ units in a ratio of 62/38 with a methoxy content of 10% by weight and a butoxy content of 5% by weight, 800 ml of methanol, and 800 ml of toluene.

The 2.0 l circulation evaporator of the second reaction unit is charged with 1800 ml of the desired alkoxypolysiloxane consisting of PhSiO$_{3/2}$ and Me$_2$SiO$_{2/2}$ units in a ratio of 62/38 with a methoxy content of 10% by weight and a butoxy content of 5% by weight, and 200 ml of toluene.

The chlorosilane in the prereactor is pumped in circulation and the temperature is kept at 20° C. The reaction units comprising the two columns are heated by means of the circulation evaporator until condensation at the top of the second column commences. Subsequently, the continuous metered additions are started as follows:

2592 g/h of a silane mixture consisting of PhSiCl$_3$ and Me$_2$SiCl$_2$ in a molar ratio of PhSiCl$_3$/Me$_2$SiCl$_2$=2/1 are fed into the prereactor. Just above the circulation evaporator of the first reaction unit, 245 g/h of water and methanol are fed in to such a degree that a constant temperature profile (of 42-55° C.) in the column is obtained (typically: approx. 50 ml/h). 160 ml/h of butanol are introduced into the distillate stream from the second reaction unit into the prereactor. The temperature in the prereactor is kept constant at 27° C.

In the bottom of reaction unit 1, the temperature is approx. 67° C. The crude product is withdrawn constantly from the circulation evaporator to the degree to which it is formed and fed to the top, below the condensation units, of reactor 2.

The temperature in the column of reactor 2 is kept at approx. 70-97° C. The temperature in the circulation evaporator of reactor 2 is approx. 180° C. The condensate from reactor unit 2 is fed into the prereactor at the bottom downstream of the circulation pump on the pressure side. Approx. 1 m above the circulation evaporator of reaction unit 2,250 ml/h of methanol and 100 ml/h of toluene are metered in.

From the circulation evaporator of reactor 2, a clear product is removed continuously. To determine the resin quality of this crude product, workup was effected with methods customary for silicone resin. The analysis of the resulting silicone resin gave a viscosity of 83 mm$^2$/s, a methoxy content of 9.8% by weight and a butoxy content of 5.1% by weight (which corresponds to a molar conversion of Si—Cl used to Si—OR of 24.4%), a PhSi/Me$_2$Si ratio of 61.6/38.4 and a molecular weight Mw of 1300 g/mol.

From the prereactor, samples were taken regularly during the continuous reaction in order to determine the SiCl conversion achieved in the prereactor. The analysis was carried out by means of NMR spectroscopy and gave, for Si—Cl, Si—O$_{1/2}$ and Si—OR, the following molar ratios: Si—Cl/Si—OR/Si—O$_{1/2}$=62.6/37.2/0.2. The analysis of the prereactor shows the particular advantage of this reaction, of introducing the distillate of the second reaction unit into the prereactor. On the basis of the stoichiometry of the end product, the maximum possible alkoxylation in the prereactor without a distillate addition of the second reaction unit could not be more than 24.4 mol % (fraction of Si—OR units based on total SiCl conversion), even taking account here of the alcohol which is required for control of the first column and for postreaction and HCl discharge in the second column. However, by virtue of the distillate of the second reaction unit being taken into account here, it is already possible to achieve a high SiCl conversion without condensation. Pure alkoxylation in the prereactor without condensation in the prereactor is preferred owing to the cleaner reaction. This prereactor design has created a capacity increased by 37% exclusively via alkoxylation based on HCl removal.

EXAMPLE 4

The prereactor is charged with 2 l of a silane mixture consisting of PhSiCl$_3$ and Me$_2$SiCl$_2$ in a molar ratio of PhSiCl$_3$/Me$_2$SiCl$_2$=2/1. The 2.5 l circulation evaporator of the first reaction unit is charged with 800 ml of the desired alkoxypolysiloxane consisting of PhSiO$_{3/2}$ and Me$_2$SiO$_{2/2}$ units in a ratio of 61/39 with a methoxy content of 10% by weight and a butoxy content of 5% by weight, 800 ml of methanol, and 800 ml of toluene.

The 2.0 l circulation evaporator of the second reaction unit is charged with 1800 ml of the desired alkoxypolysiloxane consisting of PhSiO$_{3/2}$ and Me$_2$SiO$_{2/2}$ units in a ratio of 61/39 with a methoxy content of 10% by weight and a butoxy content of 5% by weight, and 200 ml of toluene.

The chlorosilane in the prereactor is pumped in circulation and the temperature is kept at 26° C. The reaction units comprising the two columns are heated by means of the circulation evaporator until condensation at the top of the second column commences. Subsequently, the continuous metered additions are started as follows:

2592 g/h of a silane mixture consisting of PhSiCl$_3$ and Me$_2$SiCl$_2$ in a molar ratio of PhSiCl$_3$/Me$_2$SiCl$_2$=2/1 are fed into the prereactor. Just above the circulation evaporator of the first reaction unit, 170 g/h of water and methanol are fed in to such a degree that a constant temperature profile (of 54-43° C.) in the column is obtained (typically: approx. 70 ml/h). 75 g/h of water and 160 ml/h of butanol are introduced into the distillate stream from the second reaction unit into the prereactor. The temperature in the prereactor is kept constant at 26° C.

In the bottom of reaction unit 1, the temperature is approx. 69° C. The crude product is withdrawn constantly from the circulation evaporator to the degree to which it is formed and fed to the top, below the condensation units, of reactor 2.

The temperature in the column of reactor 2 is kept at approx. 66-95° C. The temperature in the circulation evaporator of reactor 2 is approx. 182° C. The condensate from reactor unit 2 is fed into the prereactor at the bottom downstream of the circulation pump on the pressure side.

Approx. 1 m above the circulation evaporator of reaction unit 2,260 ml/h of methanol and 140 ml/h of toluene are metered in.

From the circulation evaporator of reactor 2, a clear product is removed continuously. To determine the resin quality of this crude product, workup was effected with methods customary for silicone resin. The analysis of the resulting silicone resin gave a viscosity of 98 mm²/s, a methoxy content of 9.7% by weight and a butoxy content of 4.4% by weight (which corresponds to a molar conversion of Si—Cl used to Si—OMe of 23.4%), a PhSi/Me$_2$Si ratio of 60.2/39.8 and a molecular weight Mw of 1400 g/mol.

From the prereactor, samples were taken regularly during the continuous reaction in order to determine the SiCl conversion achieved in the prereactor. The analysis was carried out by means of NMR spectroscopy and gave, for Si—Cl, Si—O$_{1/2}$ and Si—OMe, the following molar ratios: Si—Cl/Si—OMe/Si—O$_{1/2}$=43.3/37.8/18.9. The analysis of the prereactor shows the particular advantage of this reaction, of introducing the distillate of the second reaction unit into the prereactor. On the basis of the stoichiometry of the end product, the maximum possible alkoxylation in the prereactor without a distillate addition of the second reaction unit could not be more than 23.4 mol % (fraction of Si—OMe units based on total SiCl conversion), even taking into account the alcohol required for control of the first column and for postreaction and HCl discharge in the second column. However, by virtue of the distillate of the second reaction unit being included, it is already possible to achieve a high SiCl conversion (greater than 37%; as in Example 3) without condensation exclusively by alkoxylation. The combination of the alkoxylation with partial condensation deburdened the downstream column by over 55% based on HCl removal.

EXAMPLE 5

The prereactor is charged with 2 l of PhSiCl$_3$. The 2.5 l circulation evaporator of the first reaction unit is charged with 1,800 ml of phenyltriethoxysilane, and 700 ml of ethanol.

The 2.0 l circulation evaporator of the second reaction unit is charged with 1800 ml of phenyltriethoxysilane, and 200 ml of ethanol.

The chlorosilane is pumped in circulation in the prereactor and heated to 50° C. The reaction units comprising the two columns are heated by means of the circulation evaporator until condensation commences at the top of the second column. Subsequently, the continuous metered additions are started as follows:

2500 g/h of PhSiCl$_3$ are fed into the prereactor. Just above the circulation evaporator of the first reaction unit, approx. 650 ml/h of ethanol are fed in. A constant temperature profile (of 50-75° C.) in the column is obtained. 1000 ml/h of ethanol are introduced into the distillate stream of the second reaction unit into the prereactor. The temperature in the prereactor is kept constant at 42° C.

In the bottom of reaction unit 1, there is a temperature of approx. 132° C. The crude product is withdrawn constantly from the circulation evaporator to the degree to which it is formed and fed to the top, below the condensation units, of reactor 2.

The temperature in the column of reactor 2 is kept at approx. 75-80° C. The temperature in the circulation evaporator of reactor 2 is approx. 182° C. The condensate from reactor unit 2 is fed into the prereactor at the bottom downstream of the circulation pump on the pressure side. Approx. 1 m above the circulation evaporator of reaction unit 2,500 ml/h of ethanol are metered in.

From the circulation evaporator of reactor 2, the clear phenyltriethoxysilane is removed continuously and still contains approx. 1 ppm of HCl. To determine the silane quality, GC and NMR analyses were carried out. It has a purity of 99.6%. 0.4% of dimer is detected.

From the prereactor, samples are taken regularly during the continuous reaction in order to determine the SiCl conversion achieved in the prereactor. The analysis was carried out by means of NMR spectroscopy and gave, for Si—Cl, Si—O$_{1/2}$ and Si—OEt, the following ratios: Si—Cl/Si—OEt/Si—O$_{1/2}$=30.2/69.5/0.3. The prereactor deburdened the downstream column by almost 70% based on HCl removal.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the continuous preparation of organosilicon compounds containing SiOC groups, comprising
    a) partially reacting one or more chlorosilanes with alcohol and optionally also with water in a prereactor to produce a partial reaction mixture;
    b) introducing said partial reaction mixture into a column first reaction unit and reacting in said first reaction unit with alcohol and optionally water to provide a crude product mixture containing volatile constitutents;
    c) transferring said crude reaction product to a column second reaction unit into which alcohol is additionally introduced and from which volatile constitutents are removed, unreactive organic solvent optionally fed to said second reaction unit; and
    d) removing SiOC-containing organosilicon end product from a lower end of said second reaction unit.

2. The process of claim 1, wherein alcohol and optionally water used in the prereactor to partially react the chlorosilane, comprises a distillate from the second reaction unit which is recycled into the prereactor in liquid or gaseous form.

3. The process of claim 2, wherein the distillate is admixed with additional alcohol and/or water in the prereactor or before introduction into the prereactor.

4. The process of claim 1, wherein the chlorosilane is a compound of the general formula

$$R_nSiCl_{4-n}$$

where
    n is 0 to 3, and where
    R is hydrogen or an identical or different monovalent, substituted or unsubstituted organic radical.

5. The process of claim 1, wherein the alcohol is an alkanol or an ether group-containing alkanol having from 1 to 6 carbon atoms.

6. The process of claim 1, wherein the unreactive organic solvent comprises at least one of toluene or xylene.

7. The process of claim 1, wherein the prereactor consists of a stirred tank, a tubular reactor, or a loop reactor, and the first and second reaction unit each consist of a column with a circulation evaporator.

8. The process of claim 1, wherein the partial reaction mixture from the prereactor is transferred into the column of a first reaction unit in which further mixing and reaction of chlorosilane, alcohols and optionally water is effected to give hydrogen chloride gas and a liquid crude product, and the liquid crude product is introduced continuously into a column used as a 2nd reaction unit, into whose lower third an alcohol is introduced.

* * * * *